(12) United States Patent
Barrilalonso et al.

(10) Patent No.: US 7,632,855 B2
(45) Date of Patent: Dec. 15, 2009

(54) PYRAZOLE COMPOUNDS AS HSP90 INHIBITORS FOR THE TREATMENT OF CANCER

(75) Inventors: Xavier Barrilalonso, Abington (GB); Brian William Dymock, Abingdon (GB); Martin James Drysdale, Abington (GB)

(73) Assignees: Vernalis (Cambridge) Limited (GB); Cancer Research Technology (GB); The Institute of Cancer (GB)

( * ) Notice: Subject to any disclaimer, the term of this patent is extended or adjusted under 35 U.S.C. 154(b) by 248 days.

(21) Appl. No.: 10/553,955

(22) PCT Filed: Apr. 23, 2004

(86) PCT No.: PCT/GB2004/001740

§ 371 (c)(1), (2), (4) Date: Aug. 10, 2006

(87) PCT Pub. No.: WO2004/096212

PCT Pub. Date: Nov. 11, 2004

(65) Prior Publication Data

US 2007/0072855 A1    Mar. 29, 2007

(30) Foreign Application Priority Data

Apr. 28, 2003  (GB) ................. 0309637.7

(51) Int. Cl.
*A61K 31/4155* (2006.01)
*C07D 231/14* (2006.01)

(52) U.S. Cl. .................. 514/406; 548/374.1
(58) Field of Classification Search ........... 548/374.1; 514/406
See application file for complete search history.

(56) References Cited

FOREIGN PATENT DOCUMENTS

| WO | WO 02/36075 A | 5/2002 |
|---|---|---|
| WO | WO 03/055860 | 7/2003 |
| WO | WO 03/055860 A1 * | 7/2003 |

* cited by examiner

*Primary Examiner*—Rei-Tsang Shiao
*Assistant Examiner*—Janet L Coppins
(74) *Attorney, Agent, or Firm*—Banner & Witcoff, Ltd.

(57) ABSTRACT

Compounds of formula (I) are inhibitors of HSP90 activity, and useful in the treatment of proliferative disease such as cancers: wherein $R_1$, $R_2$ and $R_3$ are as defined in the specification, and X is $-OR_4$ or $-NR_4R_5$ wherein $R_4$ and $R_5$ independently represent hydrogen or optionally substituted $C_1$-$C_6$ alkyl, or $R_4$ and $R_5$ taken together with the nitrogen to which they are attached form an optionally substituted nitrogen-containing ring having 5-8 ring atoms.

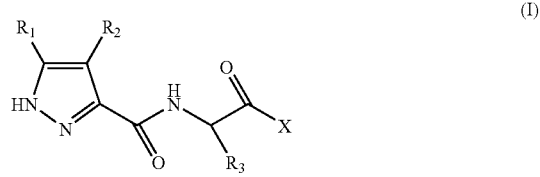

20 Claims, No Drawings

PYRAZOLE COMPOUNDS AS HSP90 INHIBITORS FOR THE TREATMENT OF CANCER

This application is a National Stage application of co-pending PCT application PCT/GB2004/001740, filed Apr. 23, 2004, which claims the priority of Great Britain Patent Application No. 0309637.7, filed Apr. 28, 2003. These applications are incorporated herein by reference in their entireties.

This invention relates to substituted pyrazoles having HSP90 inhibitory activity, to the use of such compounds in medicine, in relation to diseases which are mediated by excessive or inappropriate HSP90 activity such as cancers, and to pharmaceutical compositions containing such compounds.

BACKGROUND OF THE INVENTION

HSP90 (heat shock protein 90) is an ATP-dependent intra-cellular molecular chaperone. Due to its involvement in regulating a number of signalling pathways that are crucially important in driving the phenotype of a tumour, and the discovery that certain bioactive natural products exert their effects via HSP90 activity, the molecular chaperone HSP90 is currently regarded as a target for anticancer drug development.

BRIEF DESCRIPTION OF THE INVENTION

The present invention relates to the use of a class of substituted pyrazole compounds as HSP90 inhibitors, for example for inhibition of cancer cell proliferation. A core pyrazole ring with aromatic substitution on one ring carbon atom and a limited class of amido substitutents on another are principle characterising features of the compounds with which the invention is concerned.

DETAILED DESCRIPTION OF THE INVENTION

The invention provides the use of a compound of formula (I) or a salt, N-oxide, hydrate or solvate thereof, in the preparation of a composition for inhibition of HSP90 activity:

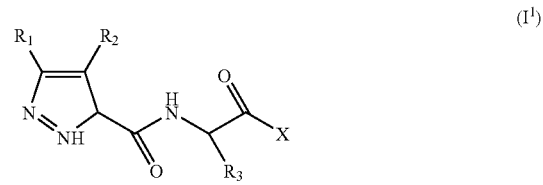

(I)

wherein
$R_1$ is a group of formula (IA):

$$-Ar^1-(Alk^1)_p-(Z)_r-(Alk^2)_s-Q \quad (IA)$$

wherein in any compatible combination
$Ar^1$ is an optionally substituted aryl or heteroaryl radical,
$Alk^1$ and $Alk^2$ are optionally substituted divalent $C_1$-$C_6$ alkylene or $C_2$-$C_6$ alkenylene radicals,
p, r and s are independently 0 or 1,
Z is —O—, —S—, —(C=O)—, —(C=S)—, —SO$_2$—, —C(=O)O—, —C(=O)NR$^A$—, —C(=S)NR$^A$—, —SO$_2$NR$^A$—, —NR$^A$C(=O)—, —NR$^A$SO$_2$— or —NR$^A$— wherein R$^A$ is hydrogen or $C_1$-$C_6$ alkyl, and Q is hydrogen or an optionally substituted carbocyclic or heterocyclic radical;
$R_2$ is (i) a group of formula (IA) as defined in relation to $R_1$;
(ii) a carboxamide radical; or
(iii) a non aromatic carbocyclic or heterocyclic ring wherein a ring carbon is optionally substituted, and/or a ring nitrogen is optionally substituted by a group of formula -(Alk$^1$)$_p$-(Z)$_r$-(Alk$^2$)$_s$-Q wherein Q, Alk$^1$, Alk$^2$, Z, p, r and s are as defined above in relation to group (IA); and
$R_3$ is hydrogen, or methyl, ethyl, n- or iso-propyl any of which being optionally substituted by hydroxy;
X is —OR$_4$ or —NR$_4$R$_5$ wherein R$_4$ and R$_5$ independently represent hydrogen or optionally substituted $C_1$-$C_6$ alkyl, or R$_4$ and R$_5$ taken together with the nitrogen to which they are attached form an optionally substituted nitrogen-containing ring having 5-8 ring atoms.

In general, the class of compounds defined above in relation to formula (I) is believed to be novel, and the invention includes all novel members of that class and their salts, hydrates and solvates.

Structure (I) above is, of course, tautomeric with structure (I$^1$), and any reference herein to one tautomer include the other

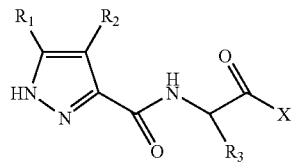

(I$^1$)

As used herein:
the term "carboxyl group" refers to a group of formula —COOH;
the term "carboxyl ester group" refers to a group of formula —COOR, wherein R is a radical actually or notionally derived from the hydroxyl compound ROH; and
the term "carboxamide group" refers to a group of formula —CONR$_a$R$_b$, wherein —NR$_a$R$_b$ is a primary or secondary (including cyclic) amino group actually or notionally derived from ammonia or the amine HNR$_a$R$_b$.

As used herein, the term "(C$_1$-C$_6$)alkyl" refers to a straight or branched chain alkyl radical having from 1 to 6 carbon atoms, including for example, methyl, ethyl, n-propyl, iso-propyl, n-butyl, isobutyl, sec-butyl, t-butyl, n-pentyl and n-hexyl.

As used herein the term "divalent (C$_1$-C$_6$)alkylene radical" means a saturated hydrocarbon chain having from 1 to 6 carbon atoms and two unsatisfied valences.

As used herein, the term "(C$_1$-C$_6$)alkenyl" refers to a straight or branched chain alkenyl radical having from 2 to 6 carbon atoms and containing at least one double bond of E or Z configuration, including for example, ethenyl and allyl.

As used herein the term "divalent (C$_2$-C$_6$)alkenylene radical" means a hydrocarbon chain having from 2 to 6 carbon atoms, at least one double bond, and two unsatisfied valences.

As used herein, the term "(C$_1$-C$_6$)alkynyl" refers to a straight or branched chain alkenyl radical having from 2 to 6 carbon atoms and containing at least one triple bond, including for example, ethynyl and prop-2-ynyl.

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "cycloalkenyl" refers to a carbocyclic radical having from 3-8 carbon atoms containing at least one double bond, and includes, for example, cyclopentenyl, cyclohexenyl, cycloheptenyl and cyclooctenyl.

As used herein the term "aryl" refers to a mono-, bi- or tri-cyclic carbocyclic aromatic radical. Illustrative of such radicals are phenyl, biphenyl and napthyl.

As used herein the term "carbocyclic" refers to a cyclic radical whose ring atoms are all carbon, and includes monocyclic aryl, cycloalkyl and cycloalkenyl radicals.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular means a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with at least one substituent selected from, for example, $(C_1-C_6)$alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, halo (including fluoro and chloro), trifluoromethyl, trifluoromethoxy, nitro, nitrile (—CN), oxo, phenyl, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1-C_6)$alkyl group. The term "optional substituent" refers to one of the foregoing substituent groups.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

Some compounds of the invention contain one or more actual or potential chiral centres because of the presence of asymmetric carbon atoms. The presence of several asymmetric carbon atoms gives rise to a number of diastereoisomers with R or S stereochemistry at each chiral centre. The invention includes all such diastereoisomers and mixtures thereof.

The Radical $R_1$

In one embodiment of the invention, $R_1$ has formula (IB):

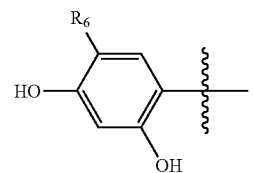

(IB)

wherein $R_6$ is chloro, bromo, $C_1-C_6$ alkyl, or cyano.

In another embodiment $R_1$ has formula (IC):

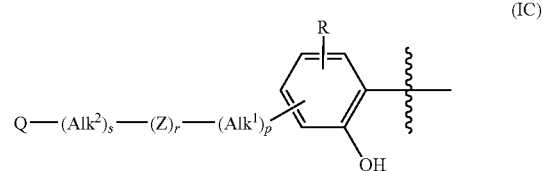

(IC)

wherein Alk$^1$, Alk$^2$, p, r, s, Z and Q are as defined in claim 1 in relation to formula (IA), and R represents one or more optional substituents. In such cases it is currently preferred that R is —OH in the 4-position of the phenyl ring and the -(Alk$^1$)$_p$-(Z)$_r$-(Alk$^2$)$_s$-Q substituent is in the 5-position of the phenyl ring. In one class of structures of type (IC), r is 0, and Q is hydrogen or optionally substituted phenyl, and in those cases s may be 0, p may be 1 and Alk$^1$ may be a non-substituted divalent $C_1-C_6$ alkylene or $C_2-C_6$ alkenylene radical, for example —CH$_2$—, —CH$_2$CH$_2$—, —CH$_2$CH$_2$CH$_2$—, or —CH═CH—. In another class of structures of type (IC), p, r and s may each be 0 and Q may be optionally substituted phenyl.

The Radical $R_2$

When $R_2$ is of type (i), i.e. a group of formula (IA), examples include phenyl, 2-, 3-, or 4-pyridyl, 2- or 3-furanyl, 2- or 3-thienyl, and thiazolyl wherein optional substituents include any of those listed above in the definition of "substituted", for example methoxy, ethoxy methylenedioxy, ethylenedioxy, fluoro, chloro, bromo, and trifluoromethyl. Currently preferred are compounds wherein $R_2$ is phenyl substituted in the 4 position by $C_1-C_6$ alkoxy such as methoxy or ethoxy, fluoro, chloro, bromo, morpholinomethyl, piperazino, N-methylpiperazino, or piperidino. Also preferred are compounds wherein $R_2$ is phenyl substituted in the 4 position by optionally substituted $C_{1-6}$ alkyl, eg optionally substituted methyl, ethyl, n-propyl or iso-propyl. Additionally preferred are compounds wherein $R_2$ is phenyl substituted in the 4 position by optionally substituted morpholino $C_{1-6}$ alkyl-, thiomorpholino $C_{1-6}$ alkyl-, piperazino $C_{1-6}$ alkyl-, methyl piperazino $C_{1-6}$ alkyl-, or diethylamino. Further preferred are compounds wherein $R_2$ is phenyl substituted in the 4 position by —NH$_2$, —NHR$^A$, —NR$^A$R$^B$, —NHCOR$^A$, —NH-COOR$^A$, —NR$^B$COOR$^A$, —NHSO$_2$OR$^A$, —NR$^B$SO$_2$OR$^A$, —NHCONH₂, —NR^A CONH₂, —NHCONR^B, —NR^A-CONHR^B, —NHCONR^A R^B or —NR^A CONR^A R^B wherein R^A and R^B are independently a (C₁-C₆)alkyl group. Still further preferred are compounds wherein R₂ is phenyl substituted in the 4 position by optionally substituted piperadino, piperazino, morpholino or thiomorpholino.

When R₂ is a carboxamide radical of type (ii) above, examples include those of formula —CONR^B(Alk)ₙR^A wherein Alk is a divalent alkylene, alkenylene or alkynylene radical, for example a —CH₂—, —CH₂CH₂—, —CH₂CH₂CH₂—, —CH₂CH=CH—, or —CH₂CCCH₂— radical, and the Alk radical may be optionally substituted, n is 0 or 1, R^B is hydrogen or a C₁-C₆ alkyl or C₂-C₆ alkenyl group, for example methyl, ethyl, n- or iso-propyl, or allyl, R^A is hydroxy or optionally substituted carbocyclic, for example hydroxy and/or chloro-substituted phenyl and 3,4 methylenedioxyphenyl; or heterocyclyl, for example pyridyl, furyl, thienyl, N-piperazinyl, or N-morpholinyl any of which heterocyclic rings may be substituted, or R^A and R^B taken together with the nitrogen to which they are attached form an N-heterocyclic ring which may optionally contain one or more additional hetero atoms selected from O, S and N, and which may optionally be substituted on one or more ring C or N atoms, examples of such N-heterocyclic rings including morpholino, piperidinyl, piperazinyl and N-phenylpiperazinyl.

The Group R₃

Presently it is preferred that R₃ be hydrogen or methyl. Preferably also, when R₃ is other than hydrogen the stereochemical configuration at the carbon centre to which it is attached is that of a D amino acid.

The Group X

In one preferred class of compounds with which the invention is concerned, X is —OR₄ or —NHR₄ wherein R₄ is C₁-C₆ alkyl, optionally substituted by hydroxy, or a primary-secondary, tertiary- or cyclic-amino group such as a morpholino, piperidinyl or piperazinyl group, the latter being optionally substituted by C₁-C₆ alkyl on the second nitrogen.

In another preferred class, X is —NR₄R₅ wherein R₄ and R₅ taken together with the nitrogen to which they are attached form a morpholino, piperidinyl or piperazinyl ring, the latter being optionally substituted by C₁-C₆ alkyl on the second nitrogen.

Specific compounds with which the invention is concerned include those of the Examples.

Compounds with which the invention is concerned may be prepared by literature methods, such as those of the preparative Examples herein, and methods analogous thereto.

Thus, compounds of formula (I) wherein X is —OR₄ may be prepared by coupling a carboxylic acid of formula (II) with an amino acid of formula (III)

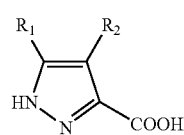

(II)

-continued

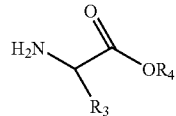

(III)

Compounds of formula (I) wherein X is —OH may be prepared by hydrolysis of the ester compound (III). Those compounds may be condensed with the amine HNR₄R₅ to prepare compounds of formula (I) wherein X is —NR₄R₅.

The compounds of the invention are inhibitors of HSP90 and are thus useful in the treatment of diseases which are mediated by excessive or inappropriate HSP90 activity such as cancers; viral diseases such as Hepatitis C (HCV) (Waxman, 2002); Immunosupression such as in transplantation (Bijlmakers, 2000 and Yorgin, 2000); Anti-inflammatory diseases (Bucci, 2000) such as Rheumatoid arthritis, Asthma, M S, Type I Diabetes, Lupus, Psoriasis and Inflammatory Bowel Disease; Cystic fibrosis (Fuller, 2000); Angiogenesis-related diseases (Hur, 2002 and Kurebayashi, 2001): diabetic retinopathy, haemangiomas, psoriasis, endometriosis and tumour angiogenesis. Also an Hsp90 inhibitor of the invention may protect normal cells against chemotherapy-induced toxicity and be useful in diseases where failure to undergo apoptosis is an underlying factor. Such an Hsp90 inhibitor may also be useful in diseases where the induction of a cell stress or heat shock protein response could be beneficial, for example, protection from hypoxia-ischemic injury due to elevation of Hsp70 in the heart (Hutter, 1996 and Trost, 1998) and brain (Plumier, 1997 and Rajder, 2000). An Hsp90 inhibitor could also be useful in diseases where protein misfolding or aggregation is a major causal factor, for example, scrapie/CJD, Huntingdon's and Alzheimer's (Sittler, 2001; Trazelt, 1995 and Winklhofer, 2001).

Accordingly, the invention also provides:

(i) a method of treatment of diseases or conditions mediated by excessive or inappropriate HSP90 activity in mammals, particularly humans, which method comprises administering to the mammal an amount of a compound of formula (I) as defined above, or a salt, hydrate or solvate thereof, effective to inhibit said HSP90 activity; and (ii) a compound of formula (I) as defined above, or a salt hydrate or solvate thereof, for use in human or veterinary medicine, particularly in the treatment of diseases or conditions mediated by excessive or inappropriate HSP90 activity;

It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy. In general, a suitable dose for orally administrable formulations will usually be in the range of 0.1 to 3000 mg once, twice or three times per day, or the equivalent daily amount administered by infusion or other routes. However, optimum dose levels and frequency of dosing will be determined by clinical trials as is conventional in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The following examples illustrate the preparation and activities of specific compounds of the invention.

EXPERIMENTAL SECTION

Scheme 1: General scheme for preparation of 5-amides

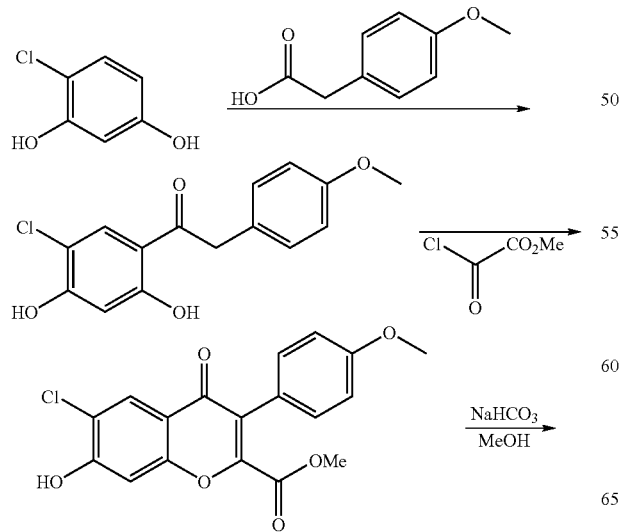

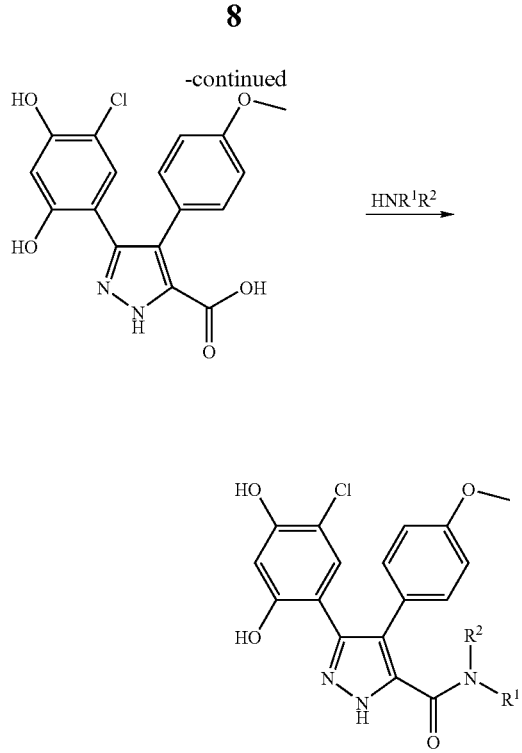

1-(5-Chloro-2,4-dihydroxy-phenyl)-2-(4-methoxy-phenyl)-ethanone

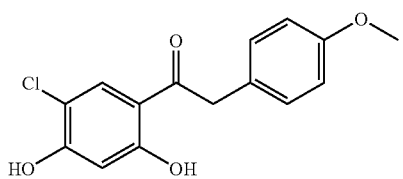

4-Chlororesorcinol (1 eq) and para-methoxyphenylacetic acid (1 eq) were combined in boron trifluoride diethyletherate (5 eq) and heated to 90° C. under nitrogen for 3 hours. The reaction was allowed to cool to room temperature and was then added drop wise to 10% NaOAc (aq). The mixture was allowed to stand overnight, and the subsequent solid was collected by vacuum filtration. The solid was dried under vacuum to give 1-5-chloro-2,4-dihydroxy-phenyl)-2-(4-methoxy-phenyl)-ethanone.

LC/MS retention time 2.485 minutes [M+H]$^+$293.2/295.2 chlorine splitting pattern.

6-Chloro-7-hydroxy-3-(4-methoxy-phenyl)-4-oxo-4H-chromene-2-carboxylic acid methyl ester

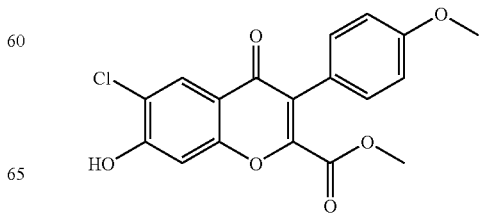

1-5-Chloro-2,4-dihydroxy-phenyl)-2-(4-methoxy-phenyl)ethanone (1 eq) was taken up in anhydrous pyridine and cooled on an ice bath to 0° C. Methyl chlorooxoacetate (3 eq) was added dropwise and the solution was stoppered and allowed to stand in the refrigerator over night.

The bright orange solution was added carefully to 100 ml 1M HCl (aq) and extracted into 2×70 ml DCM. The organic phases were combined and washed with 2×50 ml brine. All was concentrated in vacuo to a yellow solid. This was suspended in a 1:1 mixture of 1MHCl (aq) and methanol. All was heated at reflux for 4 hrs. Allowed to cool.

The reaction mixture was concentrated in vacuo to give 6-chloro-7-hydroxy-3-(4-methoxy-phenyl)-4-oxo-4H-chromene-2-carboxylic acid methyl ester as a pale yellow solid LC retention time 2.423minutes [M+H]$^+$361.2/363.2 chlorine splitting pattern.

6-Chloro-7-hydroxy-3-(4-methoxy-phenyl)-4oxo-4H-chromene-2-carboxylic acid

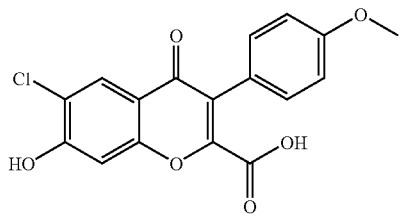

6-Chloro-7-hydroxy-3-(4-methoxy-phenyl)-4-oxo-4H-chromene-2-carboxylic acid methyl ester was taken up in a 2:1 mixture of sat. NaHCO$_3$ (aq): Methanol and all was heated at 65° C. for 5 hours. The solution was cooled to room temperature and concentrated in vacuo to remove the methanol. The residual aqueous solution was acidified with 1M HCl (aq) and a buff coloured precipitate dropped out of solution. This was collected by vacuum filtration, washed with water and with diethyl ether, to give 6-chloro-7-hydroxy-3-(4-methoxy-phenyl)-4-oxo-4H-chromene-2-carboxylic acid LC retention time 1.814 minutes 347.2/349.2 chlorine splitting pattern.

5-(5-Chloro-2,4-dihydroxy-phenyl)-4-(4-methoxy-phenyl)-2H-pyrazole-3-carboxylic acid

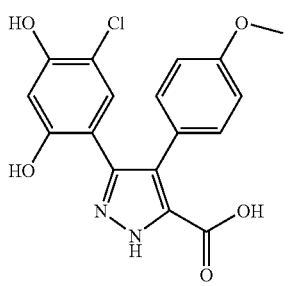

6-Chloro-7-hydroxy-3-(4methoxy-phenyl)-4-oxo-4H-chromene-2-carboxylic acid (1 eq) was taken up in ethanol and hydrazine hydrate (3 eq) was added. To aid dissolution a few drops of NaHCO3 (aq) was added, and then all was heated at 70° C. under nitrogen for 2 hours. The solution was cooled to room temperature and concentrated in vacuo to a brown oil. This was partitioned between 1MHCl(aq) and diethyl ether. The organic phases were combined, washed with 1MHCl(aq), dried over MgSO$_4$, filtered and concentrated in vacuo to give 5-(5-chloro-2,4dihydroxy-phenyl)-4-(4-methoxy-phenyl)-2H-pyrazole-3-carboxylic acid as a yellow foam.

LC retention time 2.020 min [M+H]$^+$361.2/363.2 chlorine splitting pattern.

General Synthesis of Amides

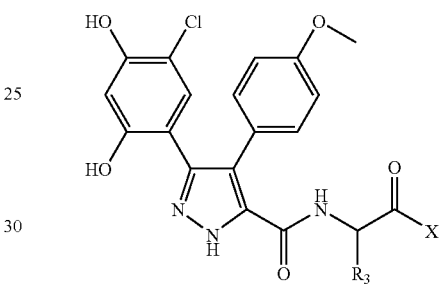

Method 1

5-(5-Chloro-2,4-dihydroxy-phenyl)-4-(4-methoxy-phenyl)-2H-pyrazole-3-carboxylic acid (1 eq) was taken up as a suspension in anhydrous dichloromethane. The resulting solution was cooled to 0° C. under nitrogen. 1-hydroxybenzotriazole hydrate (3 eq) was added, followed by N-methylmorpholine (10 eq), N-Ethyl-N'-(3dimethylaminopropyl) carbodiimide.HCl (3 eq) and amine (2 eq). All was stirred to room temperature overnight. The resulting solutions were diluted with dichloromethane and extracted with 1MHCl(aq), sat. NaHCO$_3$ (aq) and sat. NaCl (aq), then dried over MgSO$_4$, filtered and concentrated in vacuo. The residue was purified by preparative LC/MS to give the amide product.

Method 2

The acid (1 eq) was taken up in anhydrous dichloromethane and the solution was cooled to 0° C. under nitrogen. Triethylamine (6 eq) was added, followed by 4-(dimethylamino)pyridine (0.5 eq). Di-tert-butyl dicarbonate (3 eq) as a solution in anhydrous dichloromethane was added drop wise over a period of 30 minutes followed by the amine (2 eq). The reaction mixture was stirred for 2 hours at room temperature. The reaction mixture was washed with 1MHCl (aq) and then brine, and dried over MgSO$_4$. The solution was filtered and concentrated in vacuo.

The gum was dissolved in methanol. Excess 1M Na$_2$CO$_3$ (aq) was added and the solution was heated to 80° C. under nitrogen for 8 hours, then allowed to cool back to room temperature. The residue was purified by preparative LC/MS.

Scheme 2: 5-position extended amide synthesis
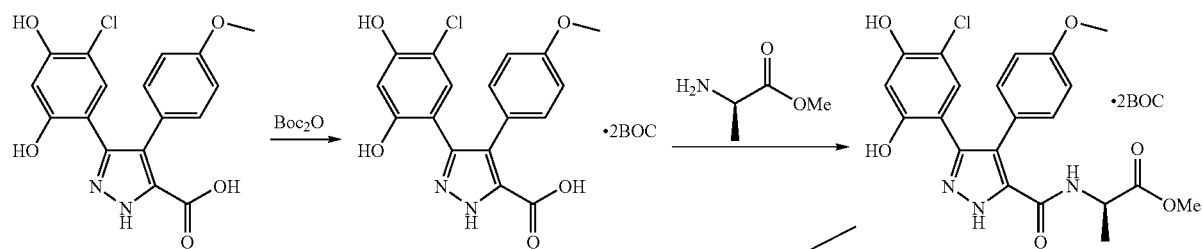
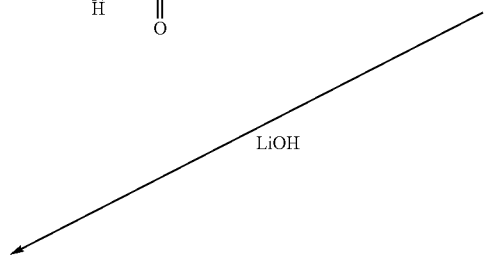
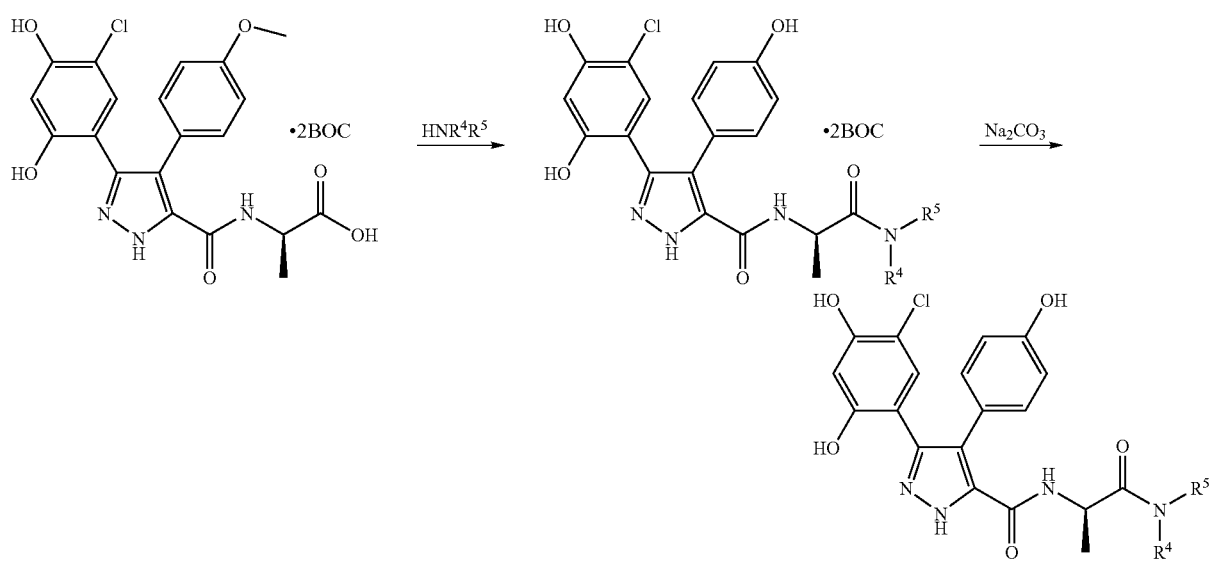

Method 3

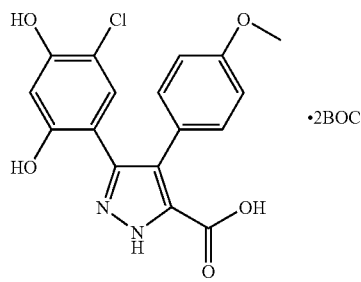

The acid (1 eq) was taken up in anhydrous dichloromethane and the solution was cooled to 0° C. under nitrogen. Triethylamine (6 eq) was added, followed by 4-(dimethylamino)pyridine (0.5 eq). Di-tert-butyl dicarbonate (3 eq) as a solution in anhydrous dichloromethane was added drop wise over a period of 30 minutes. The reaction mixture was stirred for 2 hours at room temperature. The reaction mixture was washed with 1MHCl (aq) and then brine, and dried over $MgSO_4$. The solution was filtered and concentrated in vacuo. LC/MS retention time 2.86 min $[M-Boc]^+$505.4/507.4 chlorine splitting pattern.

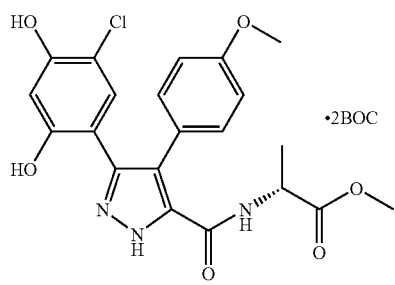

The carboxylic acid (1 eq) was dissolved in anhydrous dichloromethane. The resulting solution was cooled to 0° C. under nitrogen. 1-hydroxybenzotriazole hydrate (3 eq) was added, followed by N-methylmorpholine (8 eq), N-Ethyl-N'-(3-dimethylaminopropyl)carbodiimide.HCl (3 eq) and H-D-ALA-OMe.HCl (2 eq). All was stirred to room temperature overnight. The resulting solutions were diluted with dichloromethane and extracted with 1MHCl(aq), sat. $NaHCO_3$ (aq) and sat. NaCl (aq), then dried over $MgSO_4$, filtered and concentrated in vacuo and purified by flash chromatography (eluting with 1% MeOH-DCM). LC/MS retention time 2.97 min $[M+H]^+$646.5/648.5 chlorine splitting pattern.

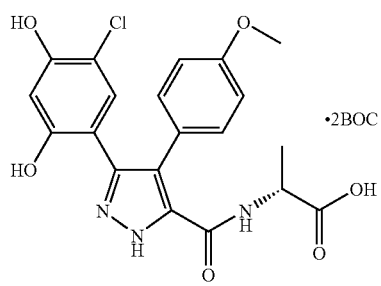

The ester (1 eq) was taken up in a 1:1 solution of water:1,4-dioxan. 1M LiOH (aq) was added and all was stirred at room temperature for 90 minutes under nitrogen.

The reaction mixture was diluted with water and washed with diethyl ether. The aqueous phase was acidified with 1M HCl (aq) and extracted into dichloromethane. The organic phase was dried over $MgSO_4$, filtered and concentrated in vacuo to give the carboxylic acid as a foam. LC/MS retention time 2.851 min 632.5/634.5

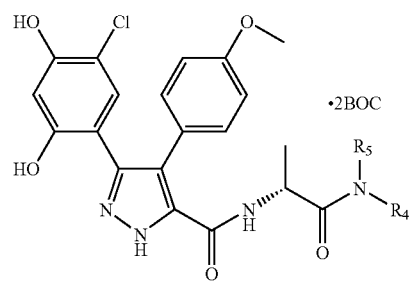

The carboxylic acid (1 eq) was dissolved in anhydrous dichloromethane. The resulting solution was cooled to 0° C. under nitrogen. 1-hydroxybenzotriazole hydrate (3 eq) was added, followed by N-methylmorpholine (8 eq), N-Ethyl-N'-(3-dimethylaminopropyl)carbodiimide.HCl (3 eq) and amine (2 eq). All was stirred to room temperature overnight. The resulting solutions were diluted with dichloromethane and extracted with 1MHCl(aq), sat. $NaHCO_3$ (aq) and sat. NaCl (aq), then dried over $MgSO_4$, filtered and concentrated in vacuo and purified by flash chromatography (eluting with 1% MeOH-DCM).

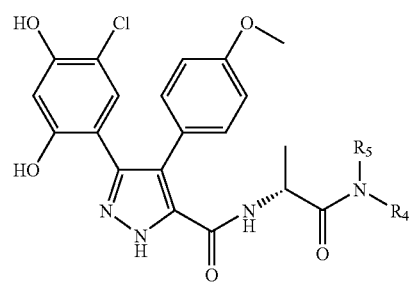

The gum was dissolved in methanol. Excess 1M $Na_2CO_3$ (aq) was added and the solution was heated to 80° C. under nitrogen for 8 hours, then allowed to cool back to room temperature. The residue was purified by preparative LC/MS.

| Example | Structure | MH+ | Synthetic Comment | Hsp90 FP IC$_{50}$ § |
|---|---|---|---|---|
| 3 | 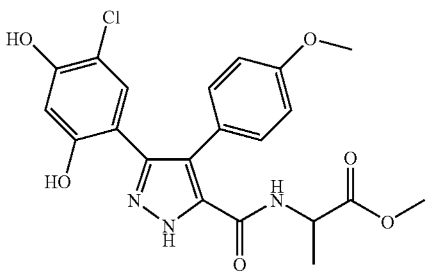 | 445<br>447 | Rac-Ala-methyl ester•HCl by Method 1 | A |
| 4 | 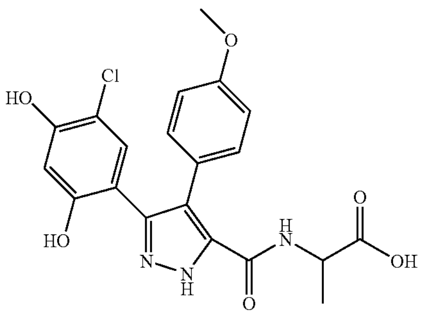 | 432<br>434 | Saponification of Example 3 at room temperature in 6:1 MeOH:5% NaOH (aq) | A |
| 6 | 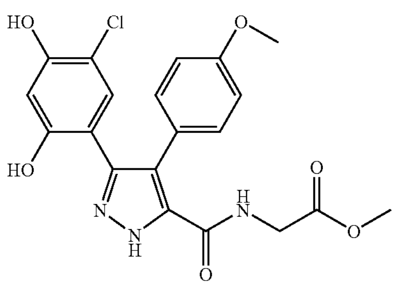 | 432<br>434 | Glycine methyl ester•HCl by Method 1 | A |
| 7 | 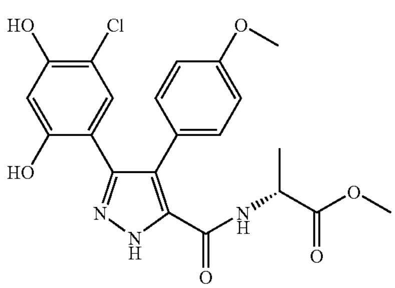 | 446<br>448 | H-D-ALA-OMe•HCl by Method 1 | A |
| 8 | 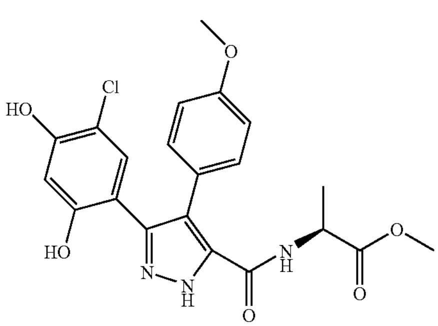 | 446<br>448 | H-ALA-OMe•HCl by Method 1 | A |

-continued

| Example | Structure | MH+ | Synthetic Comment | Hsp90 FP IC$_{50}$ § |
|---|---|---|---|---|
| 9 | 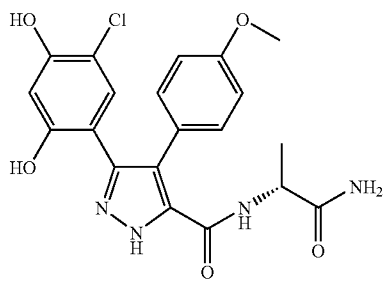 | 431 433 | H-D-ALA-NH$_2$•HCl by Method 1 | A |
| 10 | 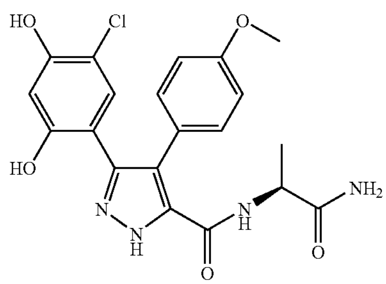 | 431 433 | H-ALA-NH$_2$•HCl by Method 1 | A |
| 12 | 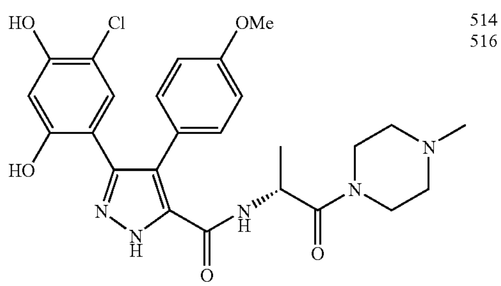 | 514 516 | Methyl piperazine by Method 3 | A |
| 13 | 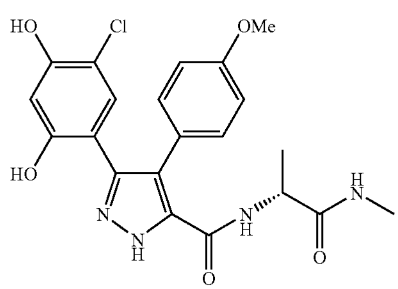 | 445 447 | Methyl amine by Method 3 | A |
| 14 | 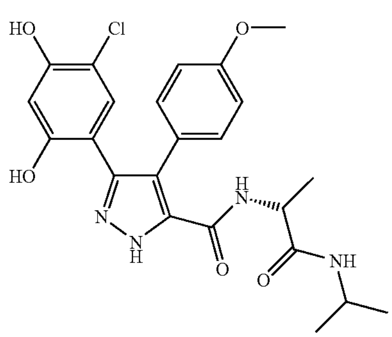 | 473 775 | Isopropylamine by Method 3 | A |

-continued

| Example | Structure | MH+ | Synthetic Comment | Hsp90 FP IC$_{50}$ § |
|---|---|---|---|---|
| 15 | (structure) | 502, 504 | Dimethylamino ethylamine by Method 3 | A |
| 16 | (structure) | 544, 546 | Morpholino-N-ethylamine by Method 3 | A |
| 18 | (structure) | 459, 461 | Ethylamine by Method 3 | A |

§ 'A' = IC50 < 10 uM in the Fluorescence Polarisation Assay described below:

Fluorescence Polarization Assay

Fluorescence polarization {also known as fluorescence anisotropy} measures the rotation of a fluorescing species in solution, where the larger molecule the more polarized the fluorescence emission. When the fluorophore is excited with polarized light, the emitted light is also polarized. The molecular size is proportional to the polarization of the fluorescence emission. The fluoroscein-labelled probe—RBT0045864-FAM—binds to HSP90 {full-length human, full-length yeast or N-terminal domain HSP90 } and the anisotropy {rotation of the probe-protein complex} is measured.

Compound is added to the assay plate, left to equilibrate and the anisotropy measured again. Any change in anisotropy is due to competitive binding of compound to HSP90, thereby releasing probe.

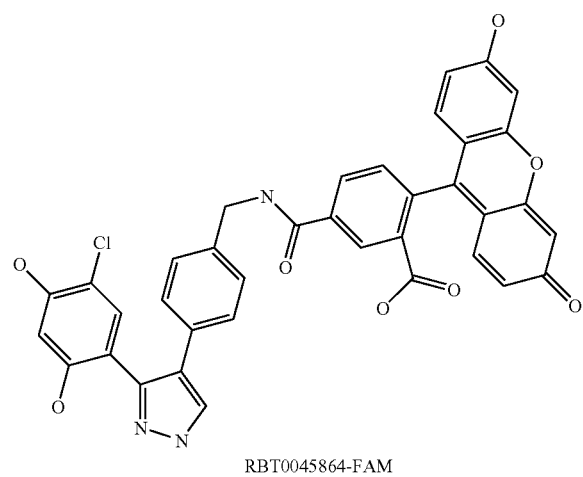

RBT0045864-FAM

Materials

Chemicals are of the highest purity commercially available and all aqueous solutions are made up in AR water.
1) Costar 96-well black assay plate #3915
2) Assay buffer of (a) 100 mM Tris pH7.4; (b) 20 mM KCl; (c) 6mM $MgCl_2$. Stored at room temperature.
3) BSA (bovine serum albumen) 10 mg/ml (New England Biolabs # B9001S)
4) 20 mM RBT0045864 (pyrazole) in 100% DMSO stock concentration. Stored in the dark at RT. Made in-house, $K_d$ ~200 µM, depending on the protein used. Working concentration is 200 nM diluted in AR water and stored at 4° C. Final concentration in assay 80 nM.
5) E. coli expressed human full-length HSP90 protein, purified >95% (see, e.g., Panaretou et al., EMBO J., Vol. 17, pp. 4829-4836, 1998) and stored in 50 µL aliquots at −80° C.

Protocol
1) Add 100 µl 1× buffer to wells 11A and 12A (=FP BLNK)
2) Prepare assay mix—all reagents are kept on ice with a lid on the bucket as the probe is light-sensitive.

|  | i. Final Conc$^n$ |  |
| --- | --- | --- |
| 1× Hsp90 FP Buffer | 10 ml | 1× |
| BSA 10 mg/ml (NEB) | 5.0 µl | 5 µg/ml |
| Probe 200 µM | 4.0 µl | 80 nM |
| Human full-length Hsp90 | 6.25 µl | 200 nM |

3) Aliquot 100 µl assay mix to all other wells
4) Seal plate and leave in dark at room temp for 20 minutes to equilibrate Compound Dilution Plate—1×3 Dilution Series
1) In a clear 96-well v-bottom plate—{# VWR 007/008/257} add 10 µl 100% DMSO to wells B1 to H11
2) To wells A1 to A11 add 17.5 µl 100% DMSO
3) Add 2.5 µl cpd to A1. This gives 2.5 mM {50×} stock cpd—assuming cpds 20 mM.
4) Repeat for wells A2 to A10. Control in columns 11 and 12.
5) Transfer 5 µl from row A to row B—not column 12. Mix well.
6) Transfer 5 µl from row B to row C. Mix well.
7) Repeat to row G.
8) Do not add any compound to row H—this is the 0 row.
9) This produces a 1×3 dilution series from 50 µM to 0.07 µM.
10) In well B12 prepare 20 µl of 100 µM standard compound.
11) After first incubation the assay plate is read on a Fusion™ a-FP plate reader (Packard BioScience, Pangboume, Berkshire, UK).
12) After the first read, 2 µl of diluted compound is added to each well for columns 1 to 10. In column 11 {provides standard curve} only add compound B11-H11. Add 2 µl of 100 mM standard cpd to wells B12-H12 {is positive control}

The Z' factor is calculated from zero controls and positive wells. It typically gives a value of 0.7-0.9.

The invention claimed is:
1. A compound of formula (I) or a salt or N-oxide thereof:

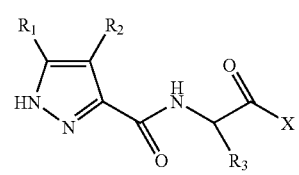

(I)

wherein
$R_1$ is a group of formula (IA):

—$Ar^1$-$(Alk^1)_p$-$(Z)_r$-$(Alk^2)_s$-Q (IA)

wherein in any compatible combination
$Ar^1$ is an optionally substituted aryl or heteroaryl radical,
$Alk^1$ and $Alk^2$ are optionally substituted divalent $C_1$-$C_6$ alkylene or $C_2$-$C_6$ alkenylene radicals,
p, r and s are independently 0 or 1,
Z is —O—, —S—, —(C=O)—, —(C=S)—, —$SO_2$—, —C(=O)O—, —C(=O)$NR^A$—, C(=S)$NR^A$—, —$SO_2NR^A$—, —$NR^AC(=O)$—, —$NR^ASO_2$— or —$NR^A$— wherein $R^A$ is hydrogen or $C_1$-$C_6$ alkyl, and
Q is hydrogen or an optionally substituted carbocyclic or heterocyclic radical;
$R_2$ is (i) a group of formula (IA) as defined in relation to $R_1$;
(ii) a carboxamide radical; or
(iii) a non aromatic carbocyclic or heterocyclic ring wherein a ring carbon is optionally substituted, and/or a ring nitrogen is optionally substituted by a group of formula -(Alk$^1$)$_p$-(Z)$_r$-(Alk$^2$)-Q wherein Q, Alk$^1$, Alk$^2$, Z, p, r and s are as defined above in relation to group (IA); and R$_3$ is hydrogen, or methyl, ethyl, n- or iso-propyl any of which being optionally substituted by hydroxy;

X is —OR$_4$ or —NR$_4$R$_5$ wherein R$_4$ and R$_5$ independently represent hydrogen or optionally substituted C$_1$-C$_6$ alkyl, or R$_4$ and R$_5$ taken together with the nitrogen to which they are attached form an optionally substituted nitrogen-containing ring having 5-8 ring atoms.

2. The compound as claimed in claim 1 wherein in the compound of formula (I), R$_1$ has formula (IB):

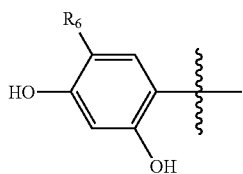

(IB)

wherein R$_6$ is chloro, bromo, C$_1$-C$_6$ alkyl, or cyano.

3. The compound as claimed in claim 1 wherein in the compound of formula (I) R$_1$ has formula (IC):

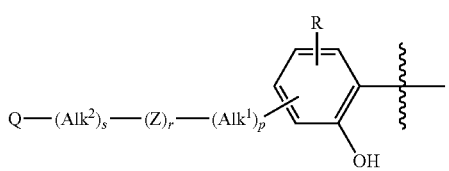

(IC)

wherein Alk$^1$, Alk$^2$, p, r, s, Z and Q are as defined in claim 1 in relation to formula (IA), and R represents one or more optional substituents.

4. The compound as claimed in claim 2 wherein R is —OH in the 4-position of the phenyl ring and the -(Alk$^1$)$_p$-(Z)$_r$-(Alk$^2$)$_s$-Q substituent is in the 5-position of the phenyl ring.

5. The compound as claimed in claim 4 wherein r is 0, and Q is hydrogen or optionally substituted phenyl.

6. The compound as claimed in claim 5 wherein s is 0, p is 1 and Alk$^1$ is a nonsubstituted divalent C$_1$-C$_6$ alkylene or C$_2$-C$_6$ alkenylene radical.

7. The compound as claimed in claim 5 wherein Alk$^1$ is —CH$_2$—, —CH$_2$CH$_2$—, —CH$_2$CH$_2$CH$_2$—, or —CH=CH—.

8. The compound as claimed in claim 4 wherein p, r and s are each 0.

9. The compound as claimed in claim 1 wherein R$_2$ is phenyl, 2-, 3-, or 4-pyridyl, 2- or 3-furanyl, 2- or 3-thienyl, or thiazolyl, optionally substituted by one or more of methoxy, ethoxy, methylenedioxy, ethylenedioxy, fluoro, chloro, bromo, or trifJuoromethyl.

10. The compound as claimed in claim 1 wherein R$_2$ is optionally substituted phenyl.

11. The compound as claimed in claim 1 wherein R$_2$ is phenyl substituted in the 4 position by (i) C$_1$-C$_6$ alkoxy such as methoxy or ethoxy, fluoro, chloro, bromo, morpholinomethyl, piperazino, N-methylpiperazino, or piperidino, (ii) optionally substituted C$_1$-C$_6$ alkyl, eg optionally substituted methyl, ethyl, n-propyl or iso-propyl (iii) optionally substituted morpholino C$_1$-C$_6$ alkyl-, thiomorpholino C$_1$-C$_6$ alkyl-, piperazino C$_1$-C$_6$ alkyl-, methyl piperazino C$_1$-C$_6$ alkyl-, or diethylamino (iv) —NH$_2$, —NHR$^A$, —NR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, NHCONHR$^B$, —NR$^A$CONHR$^B$, —NHCONR$^A$R$^B$, or —NR$^A$CONR$^A$R$^B$ wherein R$^A$ and R$^B$ are independently a (C$_1$-C$_6$) alkyl group or (v) optionally substituted piperadino, piperazino, morpholino or thiomorpholino.

12. The compound as claimed in claim 1 wherein R$_2$ is a carboxamide radical of formula —CONR$^B$(Alk)$_n$R$^A$ wherein Alk is an optionally substituted divalent alkylene, alkenylene or alkynylene radical, n is 0 or 1, R$^B$ is hydrogen or a C$_1$-C$_6$ alkyl or C$_2$-C$_6$ alkenyl group, R$^A$ is hydroxy or an optionally substituted carbocyclic or heterocyclic ring, or R$^A$ and R$^B$ taken together with the nitrogen to which they are attached form an N-heterocyclic ring which may optionally contain one or more additional hetero atoms selected from O, S and N, and which may optionally be substituted on one or more ring C or N atoms.

13. The compound as claimed claim 12 wherein

Alk is an optionally substituted —CH$_2$—, —CH$_2$CH$_2$—, —CH$_2$CH$_2$CH$_2$—, —CH$_2$CH=CH—, or —CH$_2$CCCH$_2$— radical.

n is 0 or 1,

R$^B$ is hydrogen, methyl, ethyl, n- or iso-propyl, or allyl,

R$^A$ is hydroxy, hydroxy and/or chloro-substituted phenyl, 3,4 methylenedioxyphenyl, pyridyl, furyl, thienyl, N-piperazinyl, or N-morpholinyl, or R$^A$ and R$^B$ taken together with the nitrogen to which they are attached form a morpholino, piperidinyl, piperazinyl or N-phenylpiperazinyl ring.

14. The compound as claimed in claim 12 wherein n is 0, R$^B$ is hydrogen and R$^A$ is hydroxy or an optionally substituted carbocyclic or heterocyclic ring.

15. The compound as claimed in claim 1 wherein R$_3$ is hydrogen.

16. The compound as claimed in claim 1 wherein R$_3$ is other than hydrogen and the stereochemical configuration at the carbon centre to which it is attached is that of a D amino acid.

17. The compound as claimed in claim 1 wherein X is —OR$_4$ or —NHR$_4$ wherein R$_4$ is C$_1$-C$_6$ alkyl, optionally substituted by hydroxy, or a primary- secondary, tertiary- or cyclic-amino group.

18. The compound as claimed in claim 1 wherein X is —NR$_4$R$_5$ wherein R$_4$ and R$_5$ taken together with the nitrogen to which they are attached form a morpholino, piperidinyl or piperazinyl ring, the latter being optionally substituted by C$_1$-C$_6$ alkyl on the second nitrogen.

19. A compound

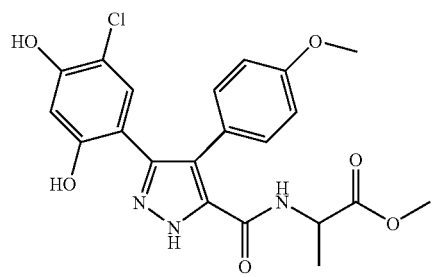

-continued
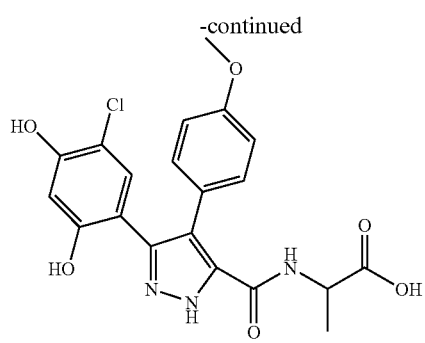
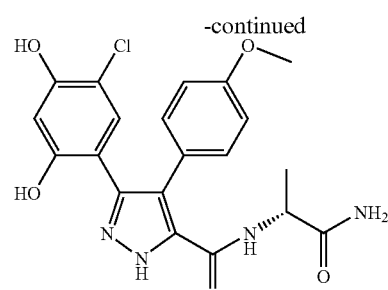
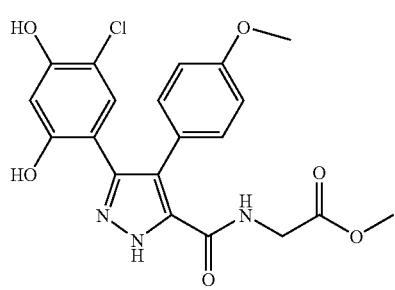
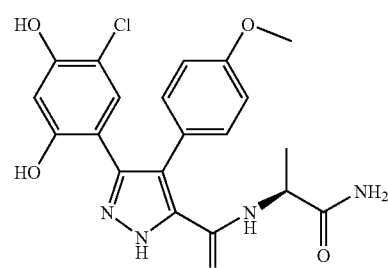
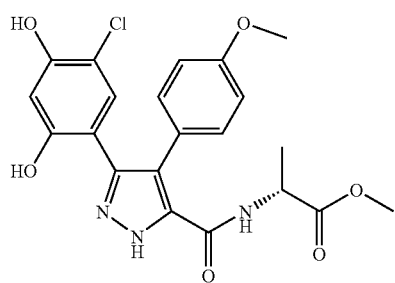
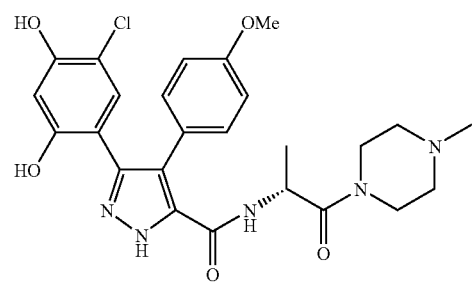
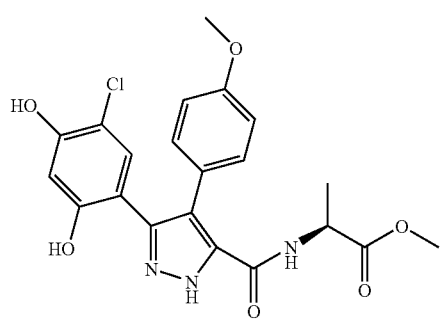
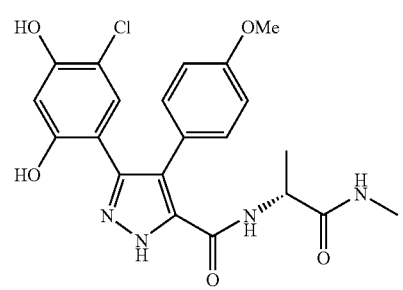

-continued
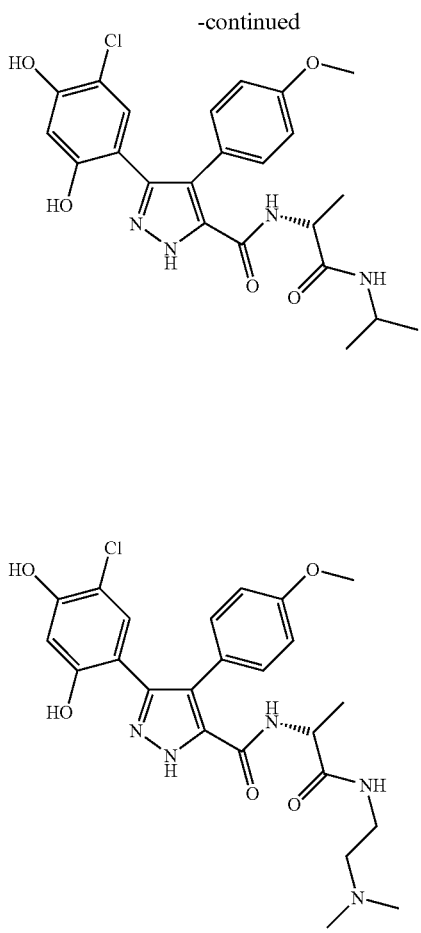
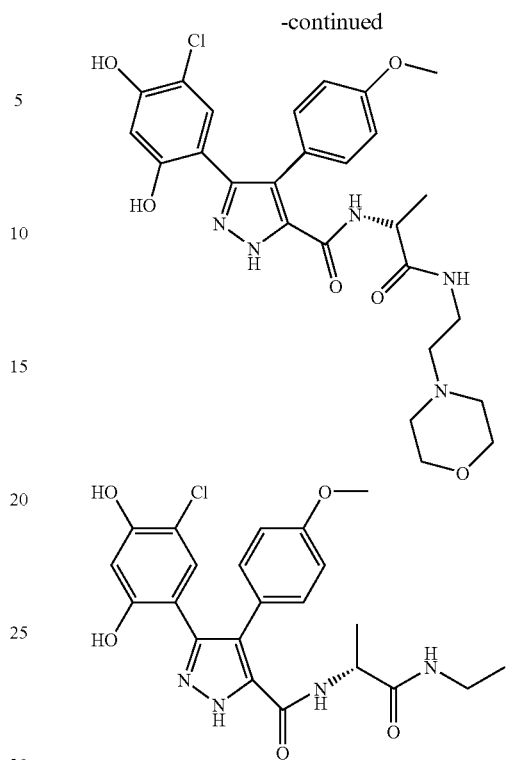
or a salt thereof.
20. A pharmaceutical or veterinary composition comprising a compound as defined in claim 1, together with a pharmaceutically or veterinarily acceptable carrier.
* * * * *